United States Patent [19]
Robert

[11] 3,932,553
[45] Jan. 13, 1976

[54] OLIGOMERIZATION OF PROPYLENE

[75] Inventor: Marcel Robert, Mont-Saint-Aignan, France

[73] Assignee: Exxon Research and Engineering Company, Linden, N.J.

[22] Filed: July 26, 1974

[21] Appl. No.: 491,998

[52] U.S. Cl................. 260/683.15 B; 260/680 R; 260/683.15 C
[51] Int. Cl.² ........................................... C07C 3/18
[58] Field of Search ........................... 260/683.15 B

[56] References Cited
UNITED STATES PATENTS

| | | |
|---|---|---|
| 2,442,644 | 6/1948 | Elwell et al. ............... 260/683.15 B |
| 2,508,744 | 5/1950 | Carlson et al. ............. 260/683.15 B |
| 2,569,383 | 9/1951 | Leyonmark et al. ........ 260/683.15 B |
| 2,588,358 | 3/1952 | Carlson et al. ............. 260/683.15 B |
| 2,766,312 | 10/1956 | Serniuk ...................... 260/683.15 B |

Primary Examiner—Paul M. Coughlan, Jr.
Attorney, Agent, or Firm—Frank T. Johmann

[57] ABSTRACT

Propylene is oligomerised in the presence of a boron trifluoride catalyst and a small amount of a reagent which reduces the activity of the catalyst, thereby resulting in a reduction of the average molecular weight of the oligomerisation product. Butadiene is one said reagent.

7 Claims, No Drawings

OLIGOMERIZATION OF PROPYLENE

The present invention relates to the manufacture of heavy olefins intended for use in particular as the raw materials for making surface-active products, plasticisers, lubricating compositions etc. It relates to a process for preparing heavy olefins from propylene. This process lends itself particularly well, but not exclusively, to the manufacture of olefins having from 15 to 21 carbon atoms per molecule. The invention also relates to the olefins that are obtained by means of this process.

Several processes are known for making propylene oligomers. These processes consist essentially of subjecting propylene to the action of appropriate catalysts. The average molecular weight of the oligomer depends on the nature of the catalyst and the conditions of temperature and pressure at which the reaction takes place. It is known, for instance, that oligomers having an average carbon chain length of 12 can be obtained by causing propylene to react on a catalyst based on phosphoric acid, at a temperature of 130° to 250°C approximately, at a pressure from 20 to 100 atmospheres, and that oligomers having an average carbon chain length of about 24 carbon atoms can be obtained by polymerising propylene in the presence of boron trifluoride, at temperatures of the order of 10° to 50°C, in the liquid phase.

Oligomerisation at high temperature on phosphoric acid, which was designed to produce preferentially propylene tetramer, indeed makes it possible to obtain the trimer, provided that the reaction is performed under suitable conditions of temperature, pressure and time, but it does not make it possible to produce in appreciable yield, oligomers higher than the tetramer.

Oligomerisation in the presence of boron trifluoride produces a mixture of olefins, the average molecular weight of which decreases as a function of the temperature at which the reaction is performed. For instance, the reaction must take place at about 30° if it is desired to obtain an oligomer having an average number of carbon atoms per molecule of about 24, but it must take place at 65° or 70°C if it is desired to obtain an oligomer having an average number of carbon atoms per molecule of about 18. Now any rise in the temperature used involves technological difficulties which are of two kinds: on the one hand, the pressure inside the reactor has to be increased, and on the other, the corrosion of the equipment is considerably accelerated.

The present invention is aimed at obviating these difficulties. It relates to a process by means of which, propylene oligomers can be obtained having a rather low average molecular weight, without its being necessary to perform the reaction at excessively high temperatures. This process is especially useful for making oligomers having an average number of carbon atoms per molecule of between 15 and 21.

This process involves the oligomerisation of propylene, catalysed by boron trifluoride, in the presence of traces of water, at a temperature of between about 0°C and 60°C, at a pressure such that the reaction mixture is liquid. According to the invention a small proportion of a reagent reducing the activity of the catalyst is added to the propylene undergoing oligomerisation. The addition of this reagent has the effect of lowering the average molecular weight of the oligomer obtained.

The applicants have discovered that diolefinic hydrocarbons or polyolefinic hydrocarbons are reagents that reduce the activity of boron trifluoride, so that the addition of a controlled quantity of these hydrocarbons in the liquid medium where the oligomerisation of the propylene takes place makes it possible to control the molecular weight of product obtained.

It is possible to use diolefinic or polyolefinic hydrocarbons, in the molecule of which the double bonds are in any position. It is possible to use in particular a hydrocarbon with cumulative double bonds, like propadiene. It is preferable to use a hydrocarbon with conjugated double bonds, such as butadiene-1-3, isoprene etc. Moreover, the molecular weight of the polyunsaturated hydrocarbon used is immaterial; the molecule of this hydrocarbon may contain 10 or 12 or more carbon atoms.

In particular, it is possible to use the mixture of unsaturated hydrocarbons that is obtained by oligomerisation of propylene at a temperature of from 130° to 250°C, at a pressure of 20 to 100 atmospheres in contact with a catalyst based on phosphoric acid, for this mixture contains a high proportion of diolefinic and polyolefinic hydrocarbons. A fraction of this mixture may also be used.

Although diolefinic or polyolefinic hydrocarbons are the preferred reagents for carrying out the invention, it is possible to consider using other reagents that are capable of reducing the activity of the catalyst. For instance, it is possible to consider using an acetylenic hydrocarbon, such as acetylene, methylacetylene etc.

The proportion of the reagent, in relation to the weight of propylene used in the reaction, is selected as a function of the molecular weight of the oligomer it is desired to obtain. A very small proportion, such for instance as 0.05% by weight in the case of dienes and polyenes, suffices to reduce considerably the molecule weight of the oligomer. As the proportion of reagent is increased, oligomers are obtained; the molecular weight of which is less and less. Nevertheless, if too high a proportion of reagent is used, the conversion of the propylene is complete. In the case of dienes and polyenes, for instance, it is for this reason preferable to use a proportion of reagent less than about 1%.

The optimum proportion of anhydrous boron trifluoride is from 0.2 to 1 part by weight approximately per 100 parts by weight of monomeric propylene. 0.5 part by weight of anhydrous boron trifluoride suffices to bring about a quantitative reaction of 100 parts of monomer, if the average period of action is about 1 hour in the reactor. It is obvious that this proportion can be increased if it is desired to reduce the average time the reaction remains in the reactor. Conversely, it is also possible to lessen the proportion of catalyst, but then it must be accepted that either the average time of treatment in the reactor is increased, or a very incomplete reaction of the propylene used is obtained.

Preferably, between 0.01 and 0.1 part by weight of water is used per 100 parts by weight of propylene.

The oligomerisation of propylene is carried out in the usual suitable reactor. This reactor has to be designed to withstand the pressure used and corrosion by boron trifluoride and by the acids derived from the hydrolysis of the latter. It must have a stirrer and the necessary means of cooling the reaction mixture and discharging the heat liberated by the reaction; it must finally be provided with the device and the additional means making it possible to incorporate the reagents and to withdraw the products from the reaction.

The raw product of the reaction includes gaseous products which consist essentially of propane, the main impurity of the propylene used as raw material, and of boron trifluoride; they are extracted from the raw product of the reaction by using the usual suitable means that are well known to the technician. After being freed from gas, the oligomer obtained still contains boron and fluorine components derived from the boron trifluoride. These compounds can be eliminated by means of the usual processes. The latter may consist in particular of washing the oligomer with an alkaline solution. It is finally possible to submit the olefins thus obtained to fractional distillation.

The average molecular weight of the olefins formed by the oligomerisation of the propylene is higher, other things being equal, the lower the temperature used. The invention makes it possible in particular to prepare oligomers; the average number of carbon atoms per molecule of which is from 15 to about 21, by performing the reaction at a temperature between 30°C and 50°C.

The following Examples are given to illustrate the description of the invention. It is obvious that these Examples are in no way restrictive.

These Examples show how the carbon chain length of the olefins obtained varies, on the one hand when the temperature at which the reaction is carried out is altered, and on the other hand when to the propylene is added a small proportion of diolefins.

To reduce the activity of the catalyst, use was made of a mixture of unsaturated hydrocarbons obtained by polymerisation of the propylene at 20°C, in contact with kieselguhr impregnated with phosphoric acid.

The different types of hydrocarbon forming this mixture was distributed as follows:

| | |
|---|---|
| Hydrocarbons of type $C_nH_{2n}$ | 80% by weight |
| Hydrocarbons of type $C_nH_{2n-2}$ | 18% by weight |
| Hydrocarbons of type $C_nH_{2n-4}$ | 2% by weight |

According to their carbon chain length, these hydrocarbons were distributed as follows:

| | |
|---|---|
| $C_{10}$ hydrocarbons | 40% by weight |
| $C_{11}$ hydrocarbons | 30% by weight |
| $C_{12}$ hydrocarbons | 20% by weight |
| Hydrocarbons heavier than $C_{12}$ | 10% by weight |

The oligomerisation of propylene was carried out at 40°C in the presence of 1.5% by weight of this mixture, i.e. in the presence of 0.3% by weight of hydrocarbons of the types $C_nH_{2n-2}$ and $C_nH_{2n-4}$. The oligomer thus obtained was compared with those obtained at 30°C and at 70°C, the addition of the polyunsaturated hydrocarbons being omitted.

The conditions of the reaction and the composition of the oligomers obtained are recapitulated in table 1 below.

TABLE 1

| Conditions of reaction | | Reference Test | | Test with addition of diolefins to propylene |
|---|---|---|---|---|
| Reaction temperature | °C | 30 | 70 | 40 |
| High purity propylene | g. | 100 | 100 | 100 |
| $BF_3$ | g. | 0.5 | 0.5 | 0.65 |
| $H_2O$ | g. | 0.05 | 0.05 | 0.05 |
| $C_nH_{2n-2}$ and $C_nH_{2n-4}$ | g. | 0 | 0 | 0.3 |
| Composition of Olefins Obtained | | | | |
| (Composition by vol.%) | | | | |
| $C_9$ | | | 2.1 | 1.2 |
| $C_{12}$ | | 0.2 | 8.5 | 2.9 |
| $C_{15}$ | | 2.9 | 24.5 | 13.6 |
| $C_{18}$ | | 9.8 | 28.8 | 28.5 |
| $C_{21}$ | | 22.0 | 20.9 | 28.7 |
| $C_{24}$ | | 29.8 | 9.6 | 16.4 |
| $C_{27}$ | | 21.5 | 3.6 | 5.6 |
| Heavier than $C_{27}$ | | 13.8 | 2.0 | 3.1 |
| Average number of carbon atoms | | 24.0 | 18.3 | 18.2 |

To carry out these Examples, the apparatus described below and shown diagrammatically in the attached drawing was used.

EXAMPLE 1

In a first series of tests, the raw material used was propylene of high purity, the composition of which was as follows: (% by weight)

| | | |
|---|---|---|
| Propylene | | 99.8 |
| Propane | | 0.2 |
| Diolefins | {propadiene and butadiene} | 0.002 |

It will be seen that the addition of 3.0% di and tri olefinic hydrocarbons makes it possible to produce at 40°C, instead of at 70°C, an oligomer having an average chain length of about 18 carbon atoms.

EXAMPLE 2

In a second series of tests, the raw material used was propylene of 95% purity (containing 5% propane and 0.002% diolefins), and butadiene-1-3 was used to reduce the activity of the catalyst.

The conditions of the reaction and the composition of the oligomers obtained are shown in the following table 2.

TABLE 2

| Conditions of Reaction | | | | |
|---|---|---|---|---|
| Reaction temperature | °C | 40 | 40 | 40 |
| 95% pure propylene | g. | 100 | 100 | 100 |
| $BF_3$ | g. | 0.75 | 0.85 | 0.85 |
| $H_2O$ | g. | 0.05 | 0.05 | 0.05 |

TABLE 2-continued

| Conditions of Reaction | | | |
|---|---|---|---|
| Butadiene g. | 0 | 0.2 | 0.4 |
| Composition of Olefins Obtained (Composition by vol.%) | | | |
| $C_9$ | — | — | 0.4 |
| $C_{12}$ | 1.5 | 2.0 | 7.3 |
| $C_{15}$ | 7.2 | 9.8 | 19.2 |
| $C_{18}$ | 16.6 | 25.3 | 30.7 |
| $C_{21}$ | 22.6 | 32.5 | 23.5 |
| $C_{24}$ | 22.4 | 21.2 | 12.3 |
| $C_{27}$ | 15.0 | 7.3 | 4.8 |
| More heavy than $C_{27}$ | 14.7 | 1.9 | 1.8 |
| Average number of carbon atoms | 23.0 | 20.7 | 19.0 |

It will be seen that at a temperature of 40°C, the addition of a very small proportion of butadiene has the effect of reducing very appreciably the carbon chain length of the oligomer obtained.

What is claimed is:

1. In a process for oligomerizing propylene comprising oligomerizing a propylene feed in the liquid phase in the presence of a boron trifluoride catalyst and traces of water at a temperature between 0°C and 60°C to form oligomers, the improvement which comprises adding to said propylene feed an amount in the range of about 0.05 to about 1 weight percent, based upon the weight of propylene, of an olefinic diene to reduce the activity of said catalyst to thereby produce oligomers having an average number of carbon atoms per molecule of between about 15 to about 21 carbon atoms.

2. A process according to claim 1, in which said diene is a hydrocarbon with conjugated double bonds.

3. A process according to claim 1, in which said diene is butadiene-1-3.

4. A process according to claim 1, in which said diene is obtained by oligomerization of propylene, at a temperature from 130°C to 250°C, under a pressure of 20 to 100 atmospheres, in contact with a catalyst based on phosphoric acid.

5. A process according to claim 1, in which 100 parts by weight of said propylene feed is contacted with 0.2 to 1 part by weight of anhydrous boron trifluoride, and from 0.01 to 0.1 part by weight of water, at a temperature of between 30°C and 50°C under a pressure such that the reaction mixture is liquid, and wherein said propylene feed contains only about 0.002% of diolefins prior to adding said 0.05 to 1 wt. % of said olefinic diene.

6. A process according to claim 5, wherein said diene is butadiene -1-3.

7. A process according to claim 5, wherein said diene is obtained by oligomerization of propylene, at a temperature of about 130°C to about 250°C, under a pressure of about 20 to 100 atmospheres, in contact with a catalyst based on phosphoric acid.

* * * * *